(12) United States Patent
Wallace et al.

(10) Patent No.: US 9,702,853 B2
(45) Date of Patent: Jul. 11, 2017

(54) METHOD FOR MONITORING CONVEYOR BELT SPLICES

(71) Applicants: Jack Bruce Wallace, Powell, OH (US); Jacques Frederick Basson, Durban (ZA)

(72) Inventors: Jack Bruce Wallace, Powell, OH (US); Jacques Frederick Basson, Durban (ZA)

(73) Assignee: Veyance Technologies, Inc., Fairlawn, OH (US)

( * ) Notice: Subject to any disclaimer, the term of this patent is extended or adjusted under 35 U.S.C. 154(b) by 14 days.

(21) Appl. No.: 14/547,396

(22) Filed: Nov. 19, 2014

(65) Prior Publication Data

US 2015/0144459 A1 May 28, 2015

Related U.S. Application Data

(60) Provisional application No. 61/908,332, filed on Nov. 25, 2013.

(51) Int. Cl.
| | |
|---|---|
| *B65G 43/00* | (2006.01) |
| *G01N 27/82* | (2006.01) |
| *B65G 43/02* | (2006.01) |
| *B65G 15/30* | (2006.01) |
| *G01L 1/12* | (2006.01) |

(52) U.S. Cl.
CPC .............. *G01N 27/82* (2013.01); *B65G 15/30* (2013.01); *B65G 43/02* (2013.01); *G01L 1/127* (2013.01)

(58) Field of Classification Search
CPC ........ B65G 43/02; G01N 27/82; G01N 27/83; G01N 27/84

USPC .......................................... 198/502.1, 810.02
See application file for complete search history.

(56) References Cited

U.S. PATENT DOCUMENTS

| | | | | |
|---|---|---|---|---|
| 3,742,477 A | | 6/1973 | Enabnit | 198/810.02 |
| 3,922,661 A | | 11/1975 | Enabnit | 198/810.02 |
| 4,020,945 A | * | 5/1977 | Takeno | B65G 43/02 |
| | | | | 198/810.02 |
| 4,439,731 A | * | 3/1984 | Harrison | G01R 33/12 |
| | | | | 324/239 |
| 4,621,727 A | | 11/1986 | Strader | 198/810.02 |
| 4,854,446 A | | 8/1989 | Strader | 198/810.02 |
| 4,864,233 A | * | 9/1989 | Harrison | G01N 27/82 |
| | | | | 324/227 |
| 5,426,362 A | * | 6/1995 | Ninnis | G01N 27/82 |
| | | | | 324/235 |

(Continued)

FOREIGN PATENT DOCUMENTS

WO     WO 2007/026135 A1     3/2007    ............. B65G 43/02

*Primary Examiner* — William R Harp
(74) *Attorney, Agent, or Firm* — Alvin T. Rockhill

(57) ABSTRACT

The present invention provides a method for detecting defects in conveyor belt splices having magnetically permeable metal cords embedded therein as the conveyor belt advances through a conveyor system, said conveyor belt having at least one splice, wherein a first set of magnetically permeable metal cords coming from a first side of the splice extend into a second side of the splice and have ends which are embedded in the second side of the splice, wherein a second set of magnetically permeable metal cords coming from the second side of the splice extend into the first side of the splice and have ends which are embedded in the first side of the splice.

19 Claims, 5 Drawing Sheets

(56) References Cited

U.S. PATENT DOCUMENTS

| | | | |
|---|---|---|---|
| 5,570,017 A * | 10/1996 | Blum | G01N 27/9026 |
| | | | 324/232 |
| 6,352,149 B1 | 3/2002 | Gartland | 198/810.02 |
| 6,715,602 B1 | 4/2004 | Gartland | 198/810.02 |
| 6,988,610 B2 | 1/2006 | Fromme et al. | 198/502.1 |
| 7,275,637 B2 * | 10/2007 | Brown | G01N 27/83 |
| | | | 198/502.1 |
| 7,740,130 B2 | 6/2010 | Wallace et al. | 198/810.02 |
| 7,810,634 B2 | 10/2010 | Wallace et al. | 198/810.02 |
| 7,894,934 B2 | 2/2011 | Wallace et al. | 700/230 |
| 7,942,258 B2 | 5/2011 | Wallace et al. | 198/810.02 |
| 8,069,975 B2 | 12/2011 | Wallace et al. | 198/810.02 |
| 8,074,789 B2 * | 12/2011 | May | B65G 43/02 |
| | | | 198/502.1 |
| 8,177,051 B2 * | 5/2012 | Alport | B65G 43/02 |
| | | | 198/810.02 |
| 8,256,607 B2 | 9/2012 | Wallace et al. | 198/810.02 |
| 8,657,105 B2 * | 2/2014 | Twigger | B65G 43/06 |
| | | | 198/502.1 |
| 8,662,290 B2 * | 3/2014 | Twigger | B65G 43/06 |
| | | | 198/810.01 |
| 2006/0202684 A1 | 9/2006 | Brown | 324/216 |

* cited by examiner

METHOD FOR MONITORING CONVEYOR BELT SPLICES

This application claims the benefit of U.S. Provisional Patent Application Ser. No. 61/908,332, filed on Nov. 25, 2013. The teachings of U.S. Provisional Patent Application Ser. No. 61/908,332 are incorporated herein by reference in their entirety.

BACKGROUND OF THE INVENTION

Conveyor belts are widely used for moving minerals, coal, and a wide variety of manufactured products from one point to another. Heavy duty conveyor belts used in mining operations can extend over distances of several miles and represent a high cost component of an industrial material handling operation. Unfortunately, such conveyor belts are susceptible to damage from the material transported thereon and a rip, slit, cut or tear may develop within the belt. For instance, sharp edges of the material being transported can gouge the surface of the belt and that can result in a rip developing. Conveyor belt segments are spliced together during installation to form a continuous loop of conveyor belting. During the operation of this conveyor belt it is susceptible to damage and the integrity of the conveyor belt and these splices can be compromised and require repairs or replacement.

In order to minimize the effects of potential longitudinal rips or transverse tears due to large cord damages, mines can utilize sensors to monitor for these conditions and alert the mine to an existing or potential catastrophic event. Conveyor belts that rip longitudinally often utilize rip detection systems to contain the damage being done by the rip in order to minimize downtime. Additionally, damaged steel cords within the conveyor belt or splice defects can be monitored and repaired proactively to avoid a catastrophic event. The cost of repairing a heavy conveyor belt and cleaning up material spilled as a result of the damage can be substantial. In cases where such damage is not detected and repaired promptly, the damage can propagate as a longitudinal rip along the length of the belt or across the width of the belt as a transverse tear with continued use of the conveyor system resulting in additional conveyor belt damage and a larger downtime event for the end user. It is accordingly desirable to detect damage to the belt and to repair the damaged area of the belt before catastrophic failure occurs. By doing so the extent of the damage to the belt can be minimized, the repair can be simplified, and the spillage of material being conveyed can be reduced or avoided and the life of the conveyor belt can be extended.

Over the years, a number of systems have been developed for detecting belt damage and for automatically stopping further movement of the belt after the damage occurs. It is well known to employ antennae within conveyor belts as part of a rip detection system. In a typical system, sensors in the form of loops of conductive wire are affixed or embedded in the belt and provide a rip detection utility as part of an overall rip detection system. Rip detection is achieved through the inferential detection of an "open circuit" condition in one or more of the sensor loops in the belt. Typically, an electrical energy source external to the belt is inductively or capacitively coupled to a sensor loop in the belt. A break in the conductive wire loop of the sensor may be detected by a remote transmitter/receiver (exciter/detector). Disposition of a plurality of such sensors at intervals along the conveyor may be effected with each sensor passing within read range of one or more exciter/detectors at various locations. A rip will encounter and damage a proximal sensor loop and the existence of the tear will be detected when the proximal sensor loop damage is detected as an open circuit by the reader at its next pass. In this manner, the existence of a rip will be promptly detected and repaired with further damage to the belt being minimized.

U.S. Pat. No. 3,742,477 discloses a "figure eight" sensor loop useful within a belt sensor system. U.S. Pat. No. 3,922,661 discloses an electronic control system for conveyor belts which monitors the condition of embedded sensor conductors in the belt and provides a warning indication and/or shutdown of the conveyor when damage occurs to the belt or control circuitry.

U.S. Pat. No. 4,621,727 discloses a reinforced conveyor belt having included therein a conductor for use in a rip monitoring system, said belt comprising: (a) an elastomeric body having an upper carrying surface and a parallel lower pulley engaging surface, each surface extending indefinitely in a direction of travel of the belt; (b) a plurality of reinforcement layers positioned within said elastomeric body; (c) a plurality of envelopes of low coefficient of friction material positioned within said elastomeric body and spaced apart in the direction of travel of the belt, wherein each envelope establishes a void area in said elastomeric body within said envelope; and (d) a shaped conductor positioned within said envelope such that said conductor is free to move within said void area during operation of said reinforced conveyor belt.

U.S. Pat. No. 4,854,446 discloses "figure eight" sensor loops disposed at intervals along a conveyor belt. This reference more specifically reveals an endless conveyor belt having a direction of travel comprising: (a) an elastomeric body having a load carrying surface and a parallel pulley engaging surface; (b) a reinforcement ply disposed within said elastomer body; and (c) a conductor, disposed within said belt in a predetermined pattern forming a closed current path; and wherein said conductor comprises a plurality of strength filaments or strands of a first metal wrapped about a conductive core of a second metal, said strength filaments or strands having a higher fatigue resistance than the conductive core, for increasing the fatigue resistance of the conductive core.

U.S. Pat. No. 6,352,149 provides a system in which antennae are embedded in a conveyor belt to couple with an electromagnetic circuit consisting of two detector heads and an electronic package. Coupling occurs only when an antenna passes across the detector heads and can only occur when the loop integrity has not been compromised. U.S. Pat. No. 6,352,149 more specifically reveals a conveyor belt incorporating within it a rip detection sensor comprising a conductor formed in an endless loop arranged in a signal inverting configuration wherein the conductor crosses itself in at least one crossing place, characterized in that: the conductor is formed as microcoil springwire; the conductor crosses itself by crossing through itself such that the microcoil springwire resides substantially in a single plane throughout the sensor including the crossing places; and means for preventing short-circuiting of the conductor at the crossing places.

U.S. Pat. No. 6,715,602 discloses a conveyor belt incorporating within it a rip detection sensor comprising a conductor formed in an endless loop, characterized in that: the belt includes at least one transponder secured to the belt in coupled relationship with the conductor; and the transponder transmits information identifying the location of the conductor along the belt.

U.S. Pat. No. 6,988,610 discloses an inspection system for detecting and reporting conditions of a conveyor belt, the system comprising: a controller comprising a splice detection program for receiving image data from at least one camera structured and arranged to capture an image of a portion of a conveyor belt, for detecting a splice in the image of the portion of the conveyor belt by processing the received image data, and for generating status information associated with the portion of the conveyor belt based on a detected splice.

International Patent Publication No. WO 2007/026135 A1 reveals a system for monitoring operation of a conveyor belt installation which comprises a conveyor belt having steel or other relatively magnetically permeable reinforcing material, said system comprising a field generator arranged in proximity to the conveyor belt to generate a magnetic field, a sensor unit arranged in proximity to the conveyor belt at a position downstream from the field generator as considered in a normal direction of belt movement, said sensor unit sensing the magnetic field emanating from the passing conveyor belt, and monitoring means to receive data related to the magnetic field properties sensed by the sensor unit during a plurality of passages of each of the length of the conveyor belt past the sensor unit, said monitoring means incorporating comparison means to compare a subsequently received set of data with an earlier received set of data, and output means to provide an output signal representative of reinforcement damage or deterioration when subsequently received data has departed from earlier received data by more than a prescribed extent.

U.S. Pat. No. 7,740,130 and U.S. Pat. No. 7,942,258 disclose a digital processor for use in a conveyor belt rip detector, which provides excitation signals at a selected frequency to inverted and non-inverted sensor loops on a conveyor belt and then, detects corresponding received signals from the sensor loops. The digital processor then performs FFTs on the corresponding received signals to provide respective received signal frequency spectrums. Next magnitude and phase values of the selected frequency in the respective received signal frequency spectrums are used to determine a qualitative state of the sensor loops. The selected frequency has a lowest detected ambient noise level, and the magnitude value is a normalized magnitude value. These patents more specifically reveal an apparatus for use in a conveyor belt rip detector that couples excitation signals to sensor loops carried by a conveyor belt and thereafter, detects corresponding received signals from respective sensor loops, the apparatus comprising: an excitation frequency generator generating excitation signals at a first frequency, the excitation signals adapted to be transmitted to the sensor loops, an analog-to-digital converter adapted to detect corresponding received signals from the sensor loops, a fast Fourier transform analyzer adapted to perform fast Fourier transforms on the corresponding received signals to provide respective signal frequency spectrums, and loop state logic determining magnitude and phase values for the first frequency in the respective received signal frequency spectrums and determining loop present and loop not present states of the sensor loops in response to determining the magnitude and phase values.

U.S. Pat. No. 7,810,634 and U.S. Pat. No. 8,256,607 disclose a monitoring system is provided for a moving conveyor belt having a plurality of embedded reinforcing cords and identification tags. A tag reader detects and identifies the identification tags passing by the tag reader while a belt monitor scans the cords to detect a plurality of magnetic reference points and a damage event of at least one cord. A control unit in communication with the belt monitor and the tag reader analyzes the belt monitor to identify the plurality of magnetic reference points and the damage event. The control unit also acquires a belt location on the moving conveyor belt from a belt map based on the detected and identified identification tag and a magnetic reference point from the plurality of magnetic reference points. When a damage event is identified, a location of the damage event is determined by the control unit based on the acquired belt location.

U.S. Pat. No. 7,894,934 discloses a remote conveyor belt monitoring system for monitoring an operation of a conveyor belt at a first geographic location. A local HMI is operable to acquire and store data representing conveyor belt conditions and operating characteristics. First and second computers at different geographic locations acquire the data via an internet. Thus, data relating to the operating conditions of the conveyor belt can be remotely consolidated and monitored by computers at different global locations. This patent more specifically reveals a method of remotely monitoring multiple conditions of a plurality of conveyor belts using a web-based diagnostic and predictive system that permits an automatic comprehensive collection and consolidation of data relating to conveyor belt health comprising: sensing conditions relating to a first operating conveyor belt at a first geographic location; generating at the first location first data in response to the conditions sensed; storing the first data in a first database at the first geographic location; acquiring the first data with a monitoring computer at a monitoring location geographically remote from the first geographic location; storing the first data in a monitoring database at the monitoring location; sensing conditions relating to a second operating conveyor belt at a second geographic location; generating at the second location second data in response to the conditions sensed; storing the second data in a second database at the second geographic location; acquiring the second data with said monitoring computer at said monitoring location geographically remote from the first and second geographic locations; storing the second data in the monitoring database at the monitoring location.

U.S. Pat. No. 8,069,975 discloses a conveyor belt rip detection system with belts having rip detection inserts that can be more easily integrated into conveyor belts at low cost. These rip detection inserts do not adversely affect the durability of the conveyor belt and can be easily replaced in the event of belt damage. This rip detection system also provides a highly reliable early image of belt damage that can facilitate quick repair before extensive belt damage occurs. U.S. Pat. No. 8,069,975 more specifically discloses a conveyor belt comprising (1) an elastomeric body having a load carrying surface and a parallel pulley engaging surface; (2) a reinforcement ply disposed within the elastomeric body; and (3) a multitude of rip detection inserts, wherein the rip detection inserts are spaced along the longitudinal length of the conveyor belt, wherein the rip detection inserts contain a multitude of rip detection wires that are comprised of a magnetically permeable material, wherein the rip detection wires are aligned in the rip detection inserts at a bias angle of 15° to 75° from being perpendicular to the longitudinal direction of the belt, and wherein the rip detection wires are spaced incrementally across the width of the belt.

Prior art rip detection panels generate issues that can either affect the integrity of the belt or the ability to replace damaged loops. Rip detection panels with wires running transversely to the conveyor belt are desirable from a manufacturing standpoint. However, such rip detection panels generate undesirable flexural properties that can result in premature failure of the conveyor belt. In any case, including rip detection loops or rip detection panels into a conveyor belt complicates the manufacturing process and adds cost to the conveyor belt. Additionally, such rip detection loops and rip detection panels do not monitor for damage in conveyor belt splices. There is accordingly a need for a reliable system to monitor for damage in conveyor belt splices. It would be even more desirable for such a system to be capable of monitoring conventional conveyor belts which do not include rip detections loops or rip detection panels. Such a system would not add additional cost to the conveyor belt per se and would not compromise the durability of the conveyor belt.

SUMMARY OF THE INVENTION

The present invention provides a system for detecting splice damage in steel cord reinforced conveyor belts. This system monitors the conveyor belt for splice damage during normal operation of the conveyor belt and can be more easily integrated into a conveyor belt system. It can be utilized in conjunction with conventional conveyor belts having standard single stage, two stage, three stage, or multiple stage (4 or more stage) splices. The monitoring system of this invention accordingly does not adversely affect the durability of the conveyor belt, does not require special sensors to be embedded in the conveyor belt and, as a result, it does not add cost to the conveyor belt system.

The conveyor belt monitoring system of this invention also provides a highly reliable means for detecting splice damage or splice anomalies before a catastrophic event has occurred. More specifically, it allows for early detection of splice damage which can facilitate quick repair before extensive splice damage occurs. The splice monitoring system of this invention also offers the advantage of being capable of ignoring damage to splices that occurred prior to a repair while continuing to monitor the belt for future splice damage. Radio frequency identification tags can also be integrated into belts used in the system of this invention to identify splices on the belt where damage has occurred by being placed in known proximity to the splice in question. The conveyor belt monitoring system of this invention can optionally include an alarm which is activated when a user defined threshold level is exceeded due to splice deterioration or new internal cord damage within the splice. In some cases it is advantageous for the system to automatically stop further movement of the conveyor belt upon detecting a specified level of change in a splice.

In accordance with this invention, splice deterioration can be measured by monitoring one or more parameters relating to belt splices including leading and trailing splice bias angles, deviation from linearity of splice angles, deviation of positive polarity and negative polarity regions of splices, and variation of center of mass of magnetic polarity positive and negative regions, center of mass of each region along belt length and across belt width, and separation of leading and trailing splice edges. In accordance with the practice of this invention tolerance windows are placed over these regions and if these tolerances are exceeded a relay is opened to provide notification of splice deterioration. This notification can be provided by an audible alarm, a visual alarm, an e-mail message, a text message, or a combination thereof. The alarm can be conveyed via a switch or relay.

The present invention more specifically discloses a method for detecting defects in conveyor belt splices having magnetically permeable metal cords embedded therein as the conveyor belt advances through a conveyor system, said conveyor belt having at least one splice, wherein a first set of magnetically permeable metal cords coming from a first side of the splice extend into a second side of the splice and have ends which are embedded in the second side of the splice, wherein a second set of magnetically permeable metal cords coming from the second side of the splice extend into the first side of the splice and have ends which are embedded in the first side of the splice, said method comprising magnetizing the first set of magnetically permeable metal cords and the second set of magnetically permeable metal cords, and monitoring the magnetic image generated by a first pole at the ends of the first set of magnetically permeable metal cords and a second pole at the ends of the second set of magnetically permeable metal cords with a magnetic sensor to detect magnetic anomalies generated by cord defects, with the proviso that if the first pole is a positive pole that the second pole is a negative pole, and with the proviso that if the first pole is a negative pole that the second pole is a positive pole. The method of this invention can be utilized for detecting defects in conveyor belts having single stage or multiple stage splices which include magnetically permeable metal cords embedded therein. In the case of multiple stage splices the magnetic images generated by a set of negative poles and a set of positive poles is monitored to detect magnetic anomalies generated by cord defects.

The subject invention further reveals a conveyor system comprising (A) a conveyor belt having magnetically permeable metal cords embedded therein, said conveyor belt having at least one splice, wherein a first set of magnetically permeable metal cords coming from a first side of the splice extend into a second side of the splice and have ends which are embedded in the second side of the splice, wherein a second set of magnetically permeable metal cords coming from the second side of the splice extend into the first side of the splice and have ends which are embedded in the first side of the splice, wherein the conveyor belt is elastomeric body having a load carrying surface and a parallel pulley engaging surface, and wherein the magnetically permeable metal cords extend longitudinally through the belt; (B) a pulley system which is adapted for receiving the pulley engaging surface of the belt; (C) a means for driving the belt along the pulley system, (D) a means for magnetizing the first set of magnetically permeable metal cords and the second set of magnetically permeable metal cords to generate by a positive pole at the ends of the first set of metal cords and a negative pole at the ends of the second set of metal cords; and (E) a means for monitoring the magnetic image generated by a positive pole at the ends of the first set of magnetically permeable metal cords and a negative pole at the ends of the second set of magnetically permeable metal cords to detect magnetic anomalies generated by cord defects.

DETAILED DESCRIPTION OF THE INVENTION

The conveyor belts which can be monitored in accordance with this invention have an elastomeric body (carcass section) with a load carrying surface on the top side thereof and a pulley engaging surface on the bottom side thereof. These conveyor belts will also include at least one reinforcement ply disposed within the elastomeric body and at least one splice making the belt an endless loop. The splices will typically connect various segments of the belt together to form an endless belt which is comprised of multiple segments which are joined together by the splices.

The splices will typically be spaced incrementally along the length of the conveyor belt. The splices are conventional splices which can be single stage splices, two stage splices, three stage splices, or multiple stage splices having four or more stages. In any case, the splices include a first set of magnetically permeable metal cords coming from a first side of the splice and which extend into the other side (a second side) of the splice. The cords coming from the first side of the splice have ends which are embedded into the other side (the second side) of the splice. Such splices also include a second set of magnetically permeable metal cords coming from the other side (the second side) of the splice and which extend into the first side of the splice. The cords coming from the second side of the splice have ends which are embedded in the first side of the splice.

The elastomeric body will normally include plies of fabric or reinforcing steel cables that typically run longitudinally within the conveyor belt. The conveyor belts of this invention can optionally also contain conventional inductive belt damage sensor loops including embedded transducer elements. Conventional rip detection systems of this type are described in U.S. Pat. No. 4,621,727, U.S. Pat. No. 4,854,446, U.S. Pat. No. 6,715,602, and U.S. Pat. No. 8,069,975. The teachings of U.S. Pat. No. 4,621,727, U.S. Pat. No. 4,854,446, U.S. Pat. No. 6,715,602, and U.S. Pat. No. 8,069,975 are incorporated herein by reference for the purpose of disclosing conventional rip detection and identification systems that can be used in conjunction with this invention. However, it may be desirable for the system of this invention to be void of rip detection loops and rip detection inserts. In any case, rip detection loops or rip detection inserts are not needed in implementing the system of this invention.

Figure 1:
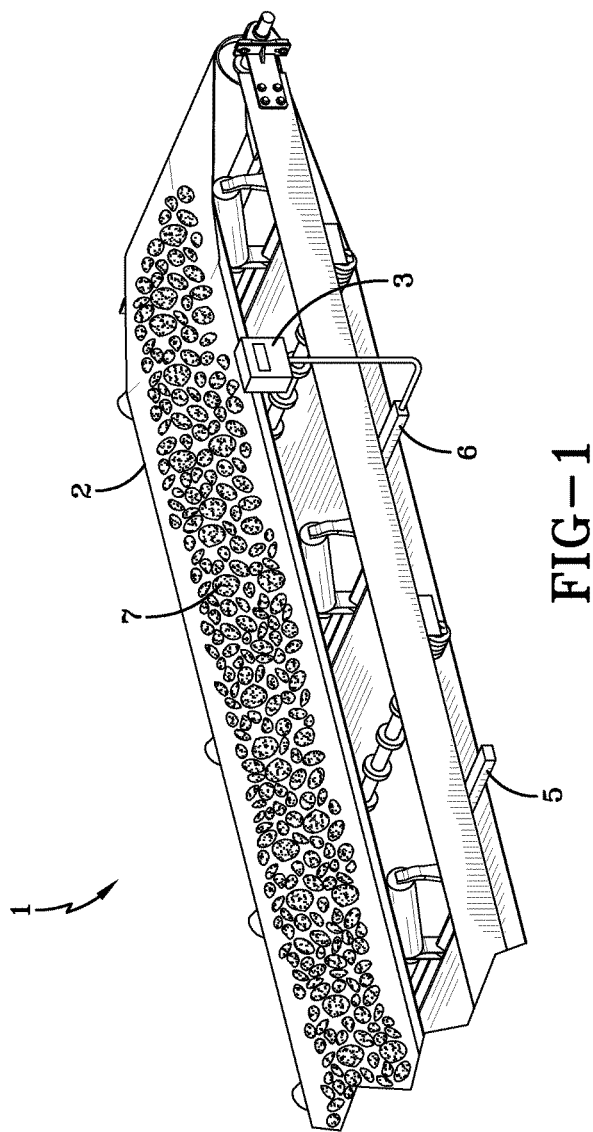
FIG. 1 is a schematic view of the conveyor belt system of this invention.

The conveyor system 1 of this invention as shown in FIG. 1 will normally include a pulley system which is adapted for receiving the pulley engaging surface 3 of the conveyor belt 2 being monitored, a means for driving the belt along the pulley system, a means for generating a magnetic field or a magnetic array 5, such as permanent magnet or an electro magnet, and a sensor array 6. In many cases it is advantageous to integrate a tachometer, proximity sensor or encoder into the conveyor system 1. Such conveyor belts can be beneficially employed in moving coal, rocks, mineral ores 7 and the like over long distances. In any case, the magnetic array 5 magnetizes steel cords 8 within the conveyor belt 2 as depicted in the case of a typical two stage splice as illustrated in FIG. 2.

Figure 2:
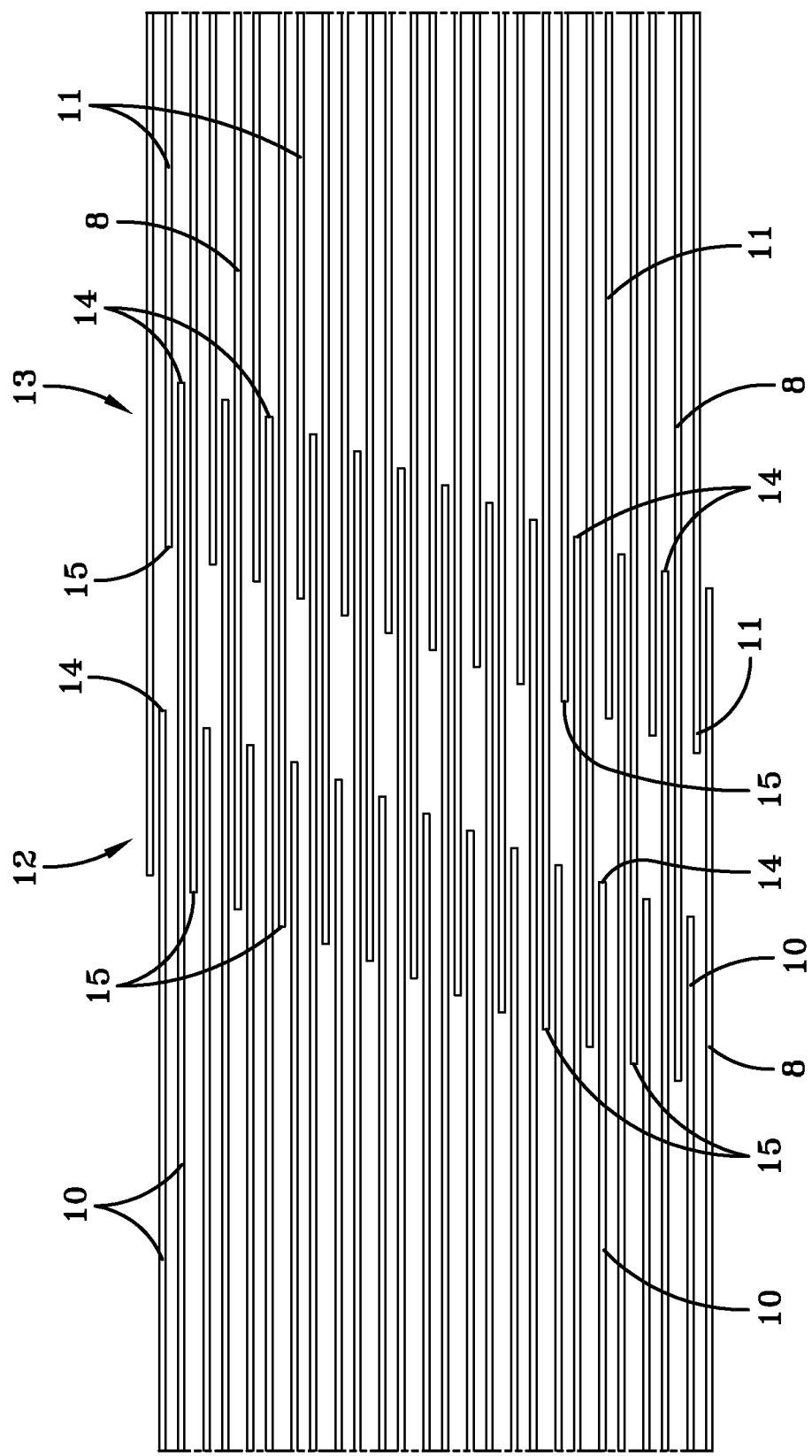
FIG. 2 illustrates the configuration of the steel cords in a conventional two stage splice.
Figure 3:
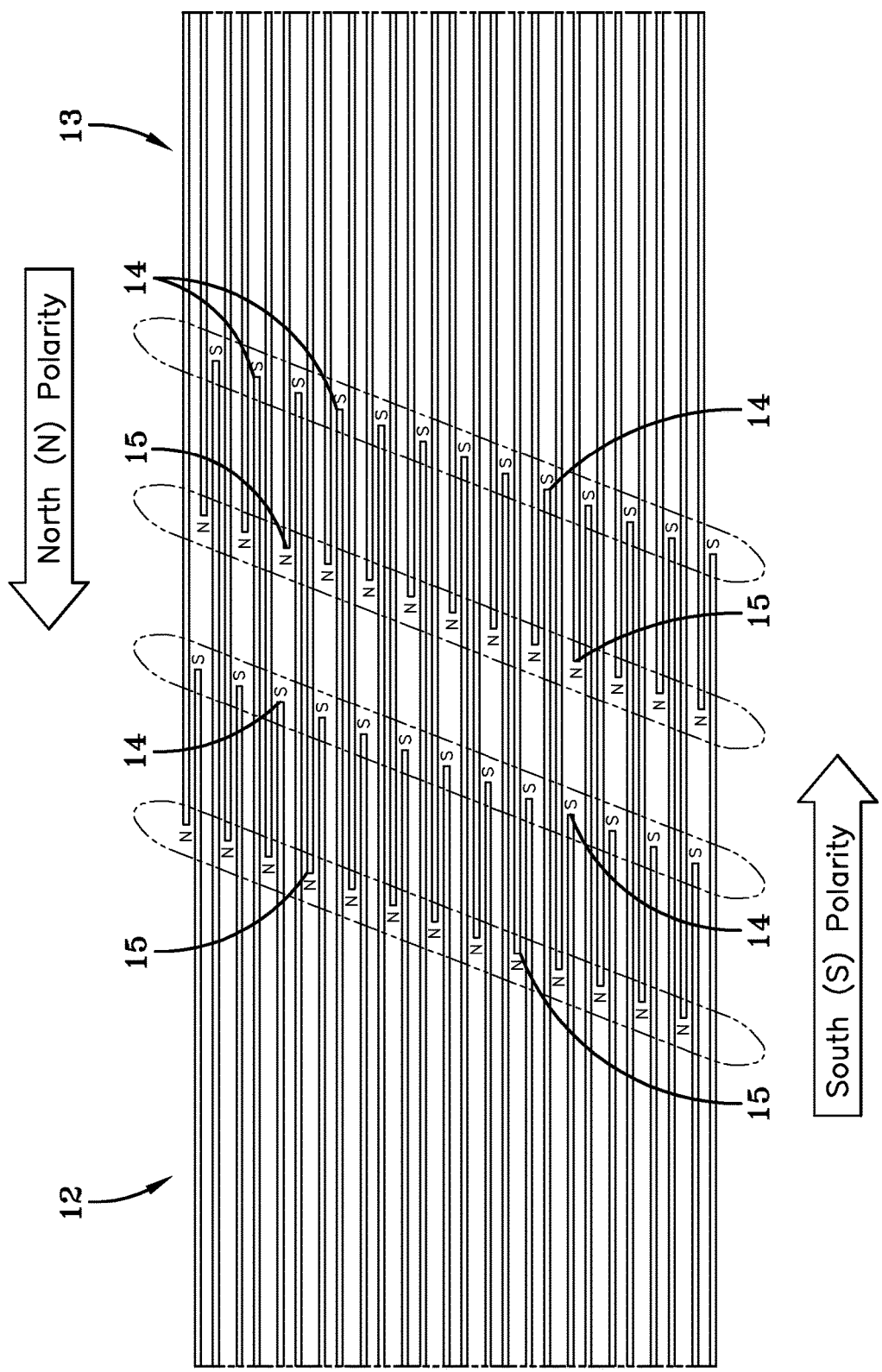
FIG. 3 shows the polarized cord ends of magnetized steel cords in a conventional two stage splice in a conveyor belt.
Figure 4:
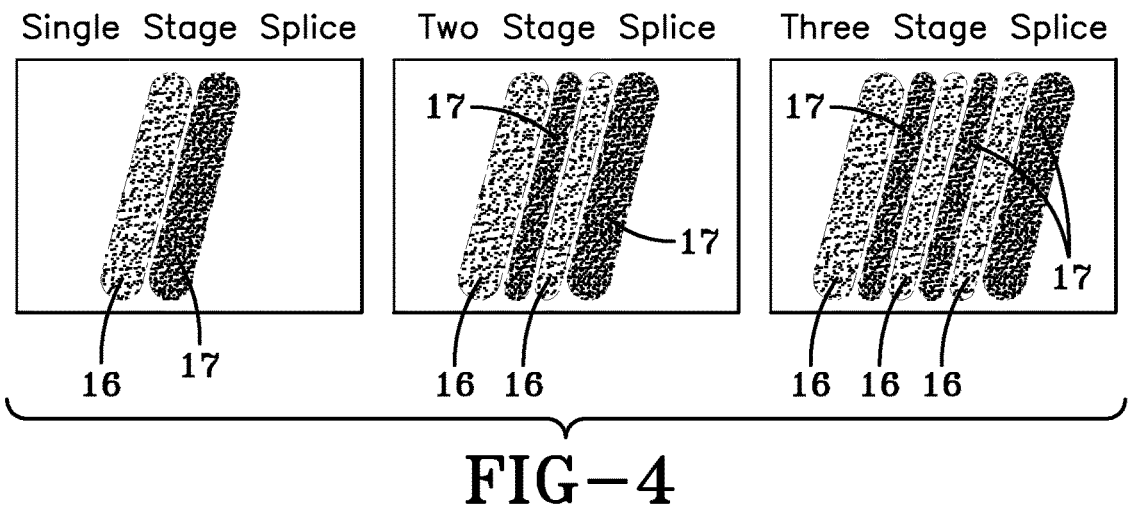
FIG. 4 is an illustration showing the magnetic images generated by single stage splices, two stage splices, and three stage splices in a conveyor belt.

A standard two stage splice is illustrated in FIG. 2. In such a two stage splice a first set of magnetically permeable metal cords 10 come from a first side of the splice 12 and extend into a second side of the splice 13 and have ends 14 which are embedded in the second side of the splice 13, wherein a second set of magnetically permeable metal cords 11 come from the second side of the splice 13 and extend into the first side of the splice 12 and have ends 15 which are embedded in the first side of the splice 12. The method of this invention can also be used in monitoring standard single stage splices, three stage, or multiple stage (4 or more stage) splices in conventional conveyor belts A magnetic array 5 magnetizes the steel cords within the conveyor belt being monitored. This magnetism of the steel cords 8 generates polarized cord ends 14 and 15 as depicted in FIG. 3. The magnetic images generated by the cord ends of conveyor belts having single stage splices, two stage splices and three stage splices are illustrated in FIG. 4. As can be seen, the single stage splices generate one north magnetic field 16 and one south magnetic field 17, the two stage splices generate two north magnetic fields 16 and two south magnetic fields 17, and the three stage splices generate three north magnetic fields 16 and three south magnetic fields 17. Belt damage in the area of a splice results in discontinuities in the geometric configuration of the magnetically permeable metal cords extending through the splice which causes a magnetic anomaly. These magnetic anomalies which are generated by the cord damage are measured using a magnetic sensor array 6 and can be displayed as an image as depicted in FIG. 4. The position of damage and splices along the length and across the width of the conveyor belt can then be accurately identified. The system can accordingly monitor steel cord belt splices over time and thereby facilitate the early detection of internal splice changes that could result in a transverse tear at the splice. This can be further facilitated by statistical analysis of splice characteristics.

Figure 5:
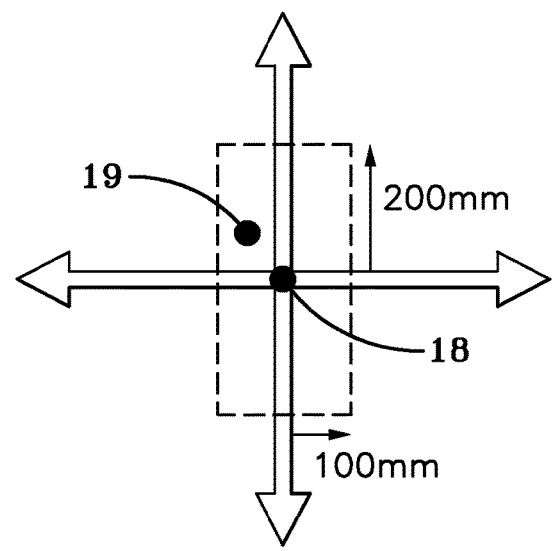
FIG. 5 is an illustration showing the position of the geometric center and the magnetic center of a conveyor belt splice which are within the threshold area of normal and acceptable operation (which does not trip an alarm).

The splice characteristics which can be monitored include, but are not limited to, the splice leading angle, the splice training angle, the straightness of the splice leading edge, the straightness of the splice trailing edge, the average separation (distance between the north magnetic field and the south magnetic field generated by the splice ends), the variation in splice symmetry along the length and width of the splice, and the center of the magnetic field of the splice as compared to the geometric center of the splice along its length and width. FIG. 5 is an illustration showing the geometric center 18 and the magnetic center 19 of a splice. Movement of the magnetic center 19 relative to the geometric center 18 of a splice over time can be evidence of splice damage occurring over that time interval.

Figure 6:
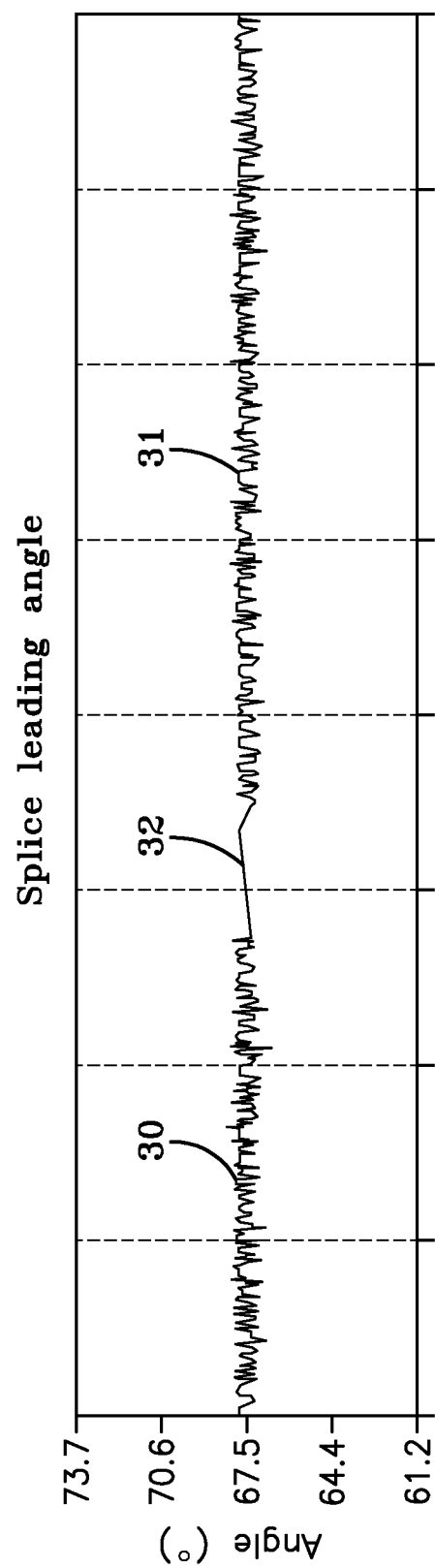
FIG. 6 is an illustration showing variation of splice leading angle as measured over a period of time.

Variation of splice leading angle as measured over a period of time is depicted in FIG. 6. A normal variation in the splice leading angle without any magnetic anomalies being depicted is shown during a first time period 30 and a second time period 31. A period during which there was no variation in the splice leading angle is shown during time period 32 occurs normally during periods when the conveyor belt is not being operated.

While certain representative embodiments and details have been shown for the purpose of illustrating the subject invention, it will be apparent to those skilled in this art that various changes and modifications can be made therein without departing from the scope of the subject invention.

What is claimed is:

1. A method for detecting defects in conveyor belt splices having magnetically permeable metal cords embedded therein as the conveyor belt advances through a conveyor system, said conveyor belt having at least one single or multiple stage splice, wherein a first set of magnetically permeable metal cords coming from a first side of the splice extend into a second side of the splice and have ends which are embedded in the second side of the splice, wherein a second set of magnetically permeable metal cords coming from the second side of the splice extend into the first side of the splice and have ends which are embedded in the first side of the splice, said method comprising magnetizing the first set of magnetically permeable metal cords and the second set of magnetically permeable metal cords, and monitoring the magnetic image generated by a first pole at the ends of the first set of magnetically permeable metal cords and a second pole at the ends of the second set of magnetically permeable metal cords with a magnetic sensor to detect magnetic anomalies generated by cord defects within the belt splices due to discontinuities in the geometric configuration of the magnetically permeable metal cords, wherein the magnetic image associated with cord ends is monitored to detect magnetic characteristic changes over time, with the proviso that if the first pole is a positive pole that the second pole is a negative pole, and with the proviso that if the first pole is a negative pole that the second pole is a positive pole.

2. The method as specified in claim 1 wherein the magnetic characteristic changes are changes in magnetic intensity, magnetic polarity, and/or magnetic geometric coordinates associated with one or more conveyor belt splices.

3. The method as specified in claim 1 wherein the magnetic characteristic is a function of splice angle.

4. The method as specified in claim 1 wherein the magnetic characteristic is a function of edge straightness.

5. The method as specified in claim 1 wherein the magnetic characteristic is a function of splice length.

6. The method as specified in claim 1 wherein the magnetic characteristic is a function of splice symmetry.

7. The method as specified in claim 1 wherein the magnetic characteristic changes are with respect to a specific splice having a magnetic center and a geometric center and wherein the magnetic characteristic changes are changes of the magnetic center of the splice relative to the geometric center of the splice.

8. A conveyor system comprising (A) a conveyor belt having magnetically permeable metal cords embedded therein, said conveyor belt having at least one single or multiple stage splice, wherein a first set of magnetically permeable longitudinal metal cords coming from a first side of the splice extend into a second side of the splice and have ends which are embedded in the second side of the splice, wherein a second set of magnetically permeable longitudinal metal cords coming from the second side of the splice extend into the first side of the splice and have ends which are embedded in the first side of the splice, wherein the conveyor belt is elastomeric body having a load carrying surface and a parallel pulley engaging surface, and wherein the magnetically permeable metal cords extend longitudinally through the belt; (B) a pulley system which is adapted for receiving the pulley engaging surface of the belt; (C) a means for magnetizing the first set of magnetically permeable metal cords and the second set of magnetically permeable metal cords to generate by a positive pole at the ends of the first set of metal cords and a negative pole at the ends of the second set of metal cords; and (D) a means for monitoring the magnetic image generated by a positive pole at the ends of the first set of magnetically permeable metal cords and a negative pole at the ends of the second set of magnetically permeable metal cords to detect magnetic anomalies generated by cord defects within the belt splices due to discontinuities in the geometric configuration of the magnetically permeable metal cords, wherein the means for monitoring the magnetic image associated with cord ends monitors to detect magnetic characteristic changes over time.

9. The conveyor system as specified in claim 8 wherein the means for monitoring the magnetic field image includes at least one magnetic sensor.

10. The conveyor system as specified in claim 8 wherein the means for monitoring the magnetic image monitors to detect splice condition as a function of splice angle.

11. The conveyor system as specified in claim 8 wherein the means for monitoring the magnetic image monitors to detect splice condition as a function of edge straightness.

12. The conveyor system as specified in claim 8 wherein the means for monitoring the magnetic image monitors to detect splice condition as a function of splice length.

13. The conveyor system as specified in claim 8 wherein the means for monitoring the magnetic image monitors to detect splice condition as a function of splice symmetry.

14. The conveyor system as specified in claim 8 wherein the means for monitoring the magnetic image monitors to detect magnetic characteristic changes over time.

15. The conveyor system as specified in claim 14 wherein the magnetic characteristic changes are changes in magnetic intensity, magnetic polarity, and/or magnetic geometric coordinates associated with one or more conveyor belt splices.

16. The conveyor system as specified in claim 14 wherein the magnetic characteristic is a function of splice angle.

17. The conveyor system as specified in claim 14 wherein the magnetic characteristic is a function of edge straightness.

18. The conveyor system as specified in claim 14 wherein the magnetic characteristic is a function of splice length.

19. The conveyor system as specified in claim 17 wherein the magnetic characteristic is a function of splice symmetry.

* * * * *